US005728579A

United States Patent [19]

Morrison et al.

[11] Patent Number: 5,728,579
[45] Date of Patent: Mar. 17, 1998

[54] DNA ENCODING MAT-8

[75] Inventors: Briggs W. Morrison, Westwood; Philip Leder, Chestnut Hill, both of Mass.

[73] Assignees: President and Fellows of Harvard College, Cambridge; The General Hospital Corporation, Boston, both of Mass.

[21] Appl. No.: 289,247

[22] Filed: Aug. 11, 1994

[51] Int. Cl.$^6$ .......................... C12N 15/11; C12N 15/63; C12N 1/21; C12N 1/19

[52] U.S. Cl. ...................... 435/325; 536/23.5; 435/320.1; 435/252.3; 435/255.1

[58] Field of Search .......................... 435/320.1, 325, 435/252.3, 252.1; 536/23.5

[56] References Cited

U.S. PATENT DOCUMENTS

| 4,383,985 | 5/1983 | Bartorelli et al. |
| 4,695,471 | 9/1987 | Fleisher et al. |
| 4,960,716 | 10/1990 | Harvey et al. |

FOREIGN PATENT DOCUMENTS

| PCT/US95/ 09762 | 9/1995 | WIPO |

OTHER PUBLICATIONS

Altenberg et al., Cancer Research, vol. 54, No. 3, issued Feb. 1, 1994, pp. 618–622.
Bear et al., "Multidrug Resistance and Cystic Fibrosis Genes:Complementarity of Function," TIG 9:67, 1993.
Ceriani et al., "Characterization of Cell Surface Antigens of Human Mammary Epithelial Cells with Monoclonal Antibodies Prepared Against Human Milk Fat Globule," Somatic Cell Genetics 9:415, 1983.
Ceriani et al., "Circulating Human Mammary Epithelial Antigens in Breast Cancer," Proc. Natl. Acad. Sci. 79:5420, 1982.
Flezar et al., "P2-Purinergic Receptors in Human Breast Tumor Cells: Coupling of Intracellular Calcium Signaling to Anion Secretion,"The Journal of Pharmacology and Experimental Therapeutics 265:1499, 1993.
Gogelein, "Chloride Channels in Epithelia," Biochimica et Biophysica Acta. 947: 521, 1988.
Greger, "Chloride Channel Blockers," Methods in Enzymology 191:793, 1990.
Gribben et al., "Bone Marrows of Non–Hodgkin's Lymphoma Patients With a BCL–2 Translocation Can Be Purged of Polymerase Chain . . . Bead Depletion,"Blood 80:1083, 1992.
Grossbard et al., "Adjuvant Immunotoxin Therapy With Anti–B4–Blocked Ricin After Autologous Bone Marrow Transplantation For Patients With B–Cell . . . Lymphoma, "Blood 81:2263, 1993.
Grossbard et al., "Serotherapy of B–Cell Neoplasms With Anti–B4–Blocked Ricin: A Phase I TRial of Daily Bolus Infusion," Blood 79:576, 1992.
Grossbard et al., "Immunotoxin Therapy of Malignancy," In DeVita et al. (eds): Important Advances In Oncology 1992. Philadelphia, PA, Lippincott, 1992, p. 111.
Moorman et al., "Phospholemman Expression Induces a Hyperpolarization–Activated Chloride Current In Xenopus Oocytes," The Journal of Biological Chemistry 267:14551, 1992.
Morrison, "The Genetics of Breast Cancer," Breast Cancer 8:15, 1994.
Soiffer et al., "Monoclonal Antibody–Purged Autologous Bone Marrow Transplanation in Adults With Acute Lymphoblastic Leukemia At High Risk of Relapse,"Bone Marrow Transplantation 12:243, 1993.
Kowdley et al., "Hyperpolarization–Activated Chloride Currents In Xenopus Oocytes," J. Gen. Physiol. 103:217, 1994.
Morrison, J. Biol Chem 270:12176, 1995.
Palmer, J. Biol Chem 266: 11126, 1991.
Moorman, J. Biol Chem 267:14551–14554, 1992.
DNA Seq Search results, p.
Lewin, Science 237;1570, 1987.
Reeh, Cell 50:667, 1987.
Desbarats, J. biol. Chem 267:19655, 1992.
Haribabu, PNAS 88:1115, 1991.

*Primary Examiner*—Lila Feisee
*Assistant Examiner*—Nancy A. Johnson
*Attorney, Agent, or Firm*—Clark & Elbing LLP

[57] ABSTRACT

A novel chloride channel protein found in human breast cancer cells is disclosed. The chloride channel protein, called Mat-8, serves as a useful diagnostic reagent for the detection of breast cancer. The Mat-8 protein and chloride channel proteins generally, are useful therapeutic targets for the treatment of breast cancer.

9 Claims, 6 Drawing Sheets

```
ccgatttctcccgaaCctctgctcagcctggtgaaccacaggccagcgtctgac                                    59

ATG CAG AAG GTG ACC CTG GGC CTG CTT GTG TTC CTG GCA GGC TTT                              104
Met Gln Lys Val Thr Leu Gly Leu Leu Val Phe Leu Ala Gly Phe

CCT GTC CTG GAC GCC AAT GAC CTA GAA GAT AAA AAC AGT CCT TTC                              149
Pro Val Leu Asp Ala Asn Asp Leu Glu Asp Lys Asn Ser Pro Phe

TAC TAT GAC AGC CTC CAG AGC CTC CAG GTT GGC GGG CTC ATC TGC GCT                          194
Tyr Tyr Asp Trp His Ser Leu Gln Val Gly Gly Leu Ile Cys Ala

GGG GTT CTG TGC GCC ATG GGC ATC ATC ATC GTC ATG AGT GCA AAA                              239
Gly Val Leu Cys Ala Met Gly Ile Ile Ile Val Met Ser Ala Lys

TGC AAA TGC AAG TTT GGC CAG AAG TCC GGT CAC CAT CCA GGG GAG                              284
Cys Lys Cys Lys Phe Gly Gln Lys Ser Gly His His Pro Gly Glu

ACT CCA CCT CTC ATC ACC CCA GGC TCA GCC CAA AGC TGA tgaggac                              336
Thr Pro Pro Leu Ile Thr Pro Gly Ser Ala Gln Ser END agaccagctgaaattgggtggaggacccgttctctgtcccccagtcctgtctctgcacag                             395
aaacttgaactccaggatggaattcttcctcctctgctggactccttgcatggcagg                                454
gcctcatctcacctctcgcaagagggtctcttgttcaatttttaatctaaaatga                                  513
ttaaaaaaaaaaaaaaaaaa
```

FIG. 1A

```
TGA GCC TGG GAT AGC TGA CAT CAG TGG GCT GCT CGA GCC GTG CTT
END Ala Trp Asp Ser END His Gln Trp Ala Ala Arg Ala Val Leu
```

FIG. 1B

```
HUMAN MAT-8    1  NDLEDKNSPFYYDWHSLQVGGLICAGVLCAMGIIIVMS
MOUSE MAT-8    1  --P-N--D-------Y--R-------I----L---VL--
CANINE PLM     1  EAPQEHD--T--YQ--RI----I----FIL--L--VL--
SHEEP γ        1  ENED------YETVRN----F-ALAFIV-LV-IL--

HUMAN MAT-8   39  AKCKCKFGQKSGHHPGETPPLITPGSAQS
MOUSE MAT-8   39  G-----R---PS-R--G------HNC
CANINE PLM    38  RR-R----N-QQRTGEPDEEEGTFRS-IRRLSTRRR
SHEEP γ       35  KRFR-GAKK-HRQI-EDGL**              **
```

FIG. 3

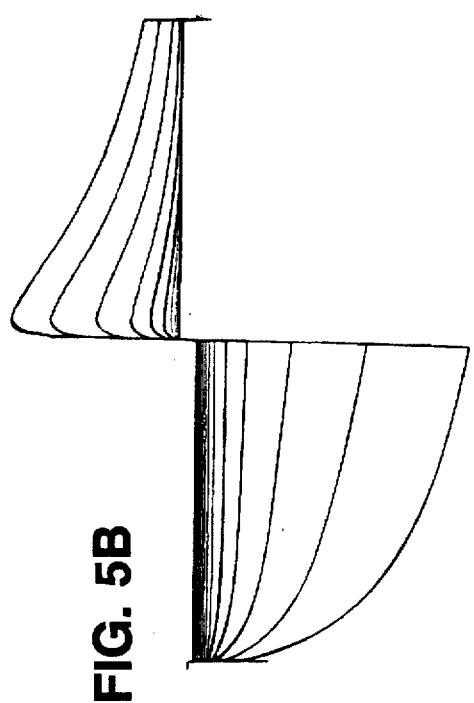
FIG. 5A
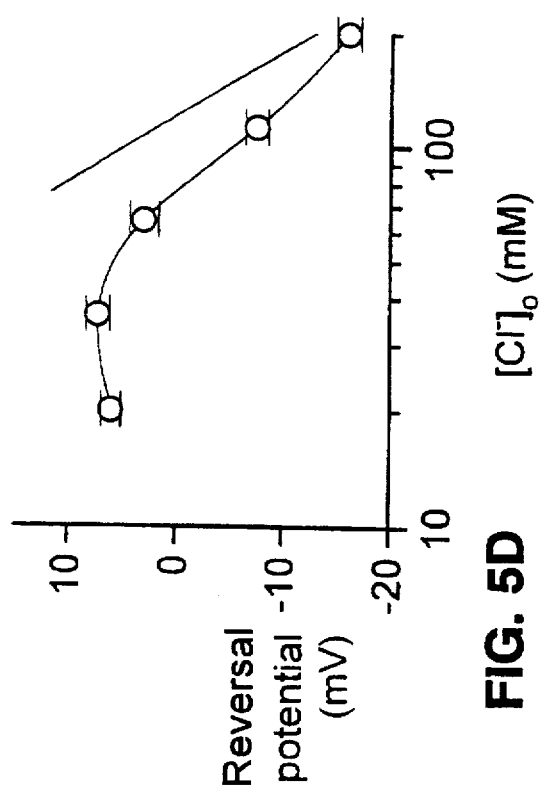
FIG. 5B
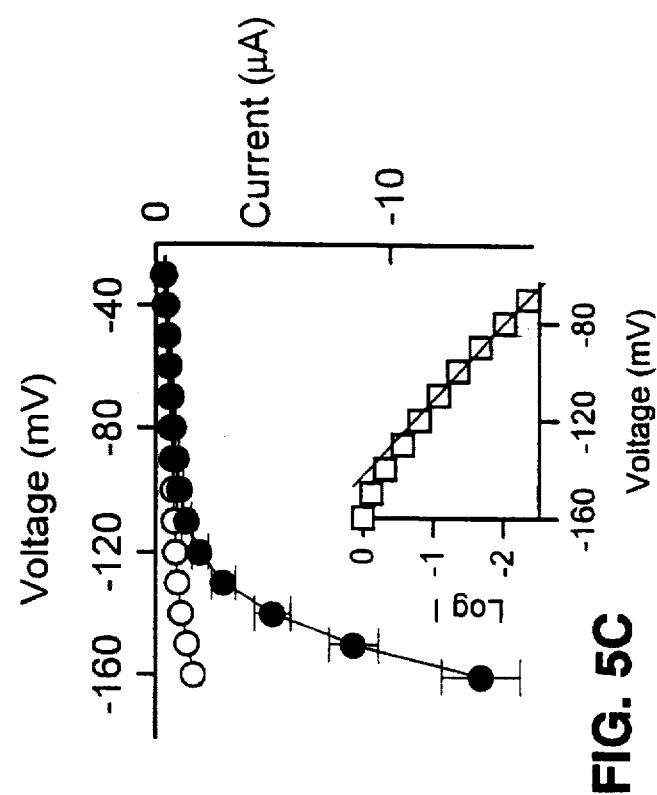
FIG. 5C
FIG. 5D

DNA ENCODING MAT-8

STATEMENT AS TO FEDERALLY SPONSORED RESEARCH

This invention was made with government support under grant numbers K11CA01578-01 and K11CAD1578-02. The U.S. government has certain rights to this invention.

BACKGROUND OF THE INVENTION

The invention relates to a novel chloride channel protein called Mat-8 which is expressed in breast cancer cells. The invention also relates to methods of detecting and treating breast cancer.

Breast cancer is a disease affecting approximately 10% of the female population (reviewed in Henderson, C. pp. 1612–1624, *Principles of Internal Medicine*, 12 ed. McGraw-Hill, Inc. (1991)). The disease, which is often fatal, is caused by the mutation of breast epithelial cell DNA. Often, one or more proto-oncogenes or anti-oncogenes are mutated. Medical research has focused on the development of non-invasive diagnostic methods to detect breast cancer at the earliest possible stage. For example, mammography has proven to be a useful non-invasive screening method for the early detection of breast cancer. Other studies have focused on identification of antigens produced by normal and malignant breast cells (Ceriani et al. *PNAS* 79, 5420 (1982); Ceriani et al. *Som. Cell Gen.* 9, 415 (1983); Bartorelli et al. U.S. Pat. No. 4,383,985; Fleisher et al. U.S. Pat. No. 4,695,471). Molecular genetic approaches have been designed to detect mutations in proto-oncogenes and anti-oncogenes, for example, the myc (e.g. c-myc, N-myc, L-myc), and Neu (i.e., erB-2 or Her-2) oncogenes, as well as the anti-oncogene p53 (Morrison, B. Hematology/Oncology Clinics of North America, 8, February 1994).

Chloride channel proteins are found in eukaryotes and prokaryotes. In eukaryotes, chloride channel proteins are generally found in epithelia capable of reabsorbing or secreting fluids. Examples of fluid-reabsorbing or secreting epithelia include the skin, urinary bladder, gallbladder, renal proximal tubule, exocrine pancreas, and the salivary gland (reviewed in Gogelein, H. BBA 521 (1988)). Chloride channel proteins play an important role in the control of ion movement across cell membranes. For example, chloride channel proteins are important to transepithelial transport, the maintenance of membrane potential, signal transduction, and the regulation of cell volume (Hille, B., (1992) *Ionic Channels of Excitable Membranes*, 2nd Ed., Sinauer Associates, Inc., Sunderland, Mass. pp 136–139 and 216–220; Thiemann, A., et al. (1992) *Nature* 356, 57–60; and Steinmayer, K., et al. (1991) *Nature* 345, 301–304). The activity of a chloride channel protein (i.e. the flux of chloride ions within a channel protein resulting in a measurable electrical current) can be modulated by hormone regulated second messenger systems, including the adenylyl cyclase-cyclic AMP (Levitan, I. B. J. *Membr. Biol.* 87, 177 (1985)) and the phospholipase C (Nishizuka, Y *Nature* 308, 693 (1984); De Lisle, R. C. and Hopfer, U *Am J. Physio.* 250, G489 (1986)) systems. Examples of chloride channel proteins include the cystic fibrosis transmembrane regulator (Bear, C. and Ling, V. *TIG* 9, 67 (1993)), phospholemman (i.e., PLM, see Moorman, J. R. et al. *J. Biol. Chem.* 14551 (1992)), the GABA and glycine receptors (Greger, R. *Meth. in Enzym.* 191, 793 (1990)), CIC-2 (Thiemann, A. et al. *Nature* 356, 57 (1992), and CIC-1 (Steinmeyer, K. et al. *Nature* 354, 301 (1991). P-glycoprotein encoded by the human MDR1 gene (i.e., multi-drug resistance gene) may function directly or indirectly as a chloride channel (Bear, C. and Ling, V. supra). Several chemical reagents and proteins are known to modulate chloride channel activity (Gogelien, H. supra; Greger, R. supra; Attall, B. et al. *Nature* 365 850 (1993)). Methods for studying the chloride conductance of chloride channel proteins produced in Xenopus oocytes have been described (Moorman, J. R. et al. (1992) *J. Biol. Chem.* 267, 14551–14554).

SUMMARY OF THE INVENTION

We have identified a novel chloride channel protein called Mat-8 (Mammary tumor, 8 Kd). The Mat-8 chloride channel protein is a useful marker for the detection of breast cancer cells or normal breast epithelia at risk of becoming malignant. The Mat-8 chloride channel protein is also selectable marker, allowing the convenient selection and removal of breast cells, especially malignant breast cells, from a biological sample. In general, chloride channel proteins such as the Mat-8 protein represent a novel therapeutic target for the treatment of breast cancer.

Accordingly, in one aspect, the invention features an isolated DNA including a DNA sequence encoding a polypeptide with at least 50% homology to the amino acid sequence shown in FIG. 1 (SEQ ID NO:4); where the polypeptide is capable of exhibiting a chloride ion current and is preferably expressed in breast cells. Preferably, the DNA sequence encodes a polypeptide consisting essentially of the amino acid sequence shown in FIG. 1 (SEQ ID NO:4). More preferably, the DNA sequence encodes a polypeptide consisting of the amino acid sequence shown in FIG. 1 (SEQ ID NO:4).

The invention also features the isolated DNA included within a vector. The vector may be provided as a purified preparation (e.g., a vector separated from a mixture of vectors which make up a genomic or cDNA library). Preferably, the vector is included in a cell. The cell may be a prokaryotic (e.g., *E. coli*), a eukaryotic (e.g., a Xenopus oocyte, yeast cell or mammalian cell) or an insect cell (e.g. a cell derived from *Spodoptera frugiperda* or *Trichoplusia ni*). Preferably, the cell expresses a polypeptide of the invention, and exhibits a chloride ion current.

In another aspect, the invention features a substantially pure DNA having the sequence of FIG. 1 (SEQ ID NO:2), or degenerate variants thereof, and encoding the amino acid sequence shown in FIG. 1 (SEQ ID NO:4).

In another aspect, the invention features a substantially pure DNA which a) is capable of hybridizing to the DNA sequence of FIG. 1 (SEQ ID NO: 2) under high stringency hybridization conditions; and b) encodes a polypeptide having a biological activity of the Mat-8 protein.

The invention also features a single-stranded oligonucleotide primer complementary to a portion of the DNA sequence depicted in FIG. 1 (SEQ ID NO:2), where the primer is either DNA or RNA and is at least 12 nucleotides in length, preferably the oligonucleotide primer is between 12 and 50 nucleotides (inclusive) in length.

The invention also features a substantially pure preparation of polypeptide produced by expressing an isolated DNA encoding a polypeptide with at least 50% homology to the amino acid sequence shown in FIG. 1 (SEQ ID NO:4); where the polypeptide is capable of exhibiting a chloride ion current and is preferably expressed in breast cells.

The invention also features a method of manufacturing a polypeptide of the invention, the method including the steps of:

a) providing a cell which includes an isolated DNA encoding a polypeptide;

b) culturing the cell in medium under conditions which permit expression of the polypeptide; and c) purifying the polypeptide from the cell or the medium.

The invention also features an antibody, preferably a monoclonal antibody, capable of specifically forming an immune complex with a substantially pure polypeptide encoded by an isolated DNA which includes a DNA sequence with at least 50% homology to the amino acid sequence shown in FIG. 1 (SEQ ID NO: 4), where the polypeptide is capable of exhibiting a chloride ion current and is preferably expressed in breast cells. Antibodies of the invention include those which are capable of inhibiting the activity of a polypeptide of the invention.

The invention also features a cell, preferably a homogenous population of cells, which includes an isolated DNA encoding a polypeptide with at least 50% homology to the amino acid sequence shown in FIG. 1 (SEQ ID NO:4) where the polypeptide is capable of exhibiting a chloride ion current and is preferably expressed in breast cells. The cell may be a prokaryotic (e.g., *E. coli*), a eukaryotic (e.g., a Xenopus oocyte, yeast cell or mammalian cell) or an insect cell (e.g. a cell derived from *Spodoptera freugiperda* or *Trichoplusia ni*). Preferably, the cell expresses a polypeptide of the invention and exhibits a chloride ion current.

In another aspect, the invention features a method for detecting breast cancer cells in a biological sample, including the steps of:

a) contacting the biological sample with an antibody, preferably a monoclonal antibody, capable of specifically forming an immune complex with a substantially pure polypeptide with at least 50% homology to the amino acid sequence shown in FIG. 1 (SEQ ID NO: 4), where the polypeptide is capable of exhibiting a chloride ion current and is preferably expressed in breast cells; the contacting being under conditions which permit the formation of an immune complex between the antibody and any of the polypeptide present in the biological sample; and b) detecting an increased level of the immune complex as an indication of the presence of breast cancer cells in the biological sample.

In a preferred embodiment, the biological sample is from a human, preferably a human bone marrow, blood, or breast tissue sample.

In another aspect, the invention features a method of determining whether a compound is capable of modulating the activity of a chloride channel protein, the method including the steps of:

a) contacting the compound with a cell which includes an isolated DNA including a DNA sequence encoding a polypeptide with a least 50% homology to the amino acid sequence shown in FIG. 1 (SEQ ID NO: 4), the cell expressing the polypeptide and exhibiting a chloride ion current;

b) detecting an altered chloride ion current, preferably an inhibition of the chloride ion current, as an indication that the compound modulates the activity of the chloride channel protein.

In preferred embodiments, the cells are Xenopus oocytes; the compound capable of modulating the chloride ion current is SITS; and the chloride channel protein consists essentially of the amino acid sequence shown in FIG. 1 (SEQ ID NO: 4).

In another aspect, the invention features a method of inhibiting breast tumor growth in a mammal, preferably a human, the method including administering to the mammal a therapeutic amount of a compound capable of modulating the activity of a chloride channel protein.

In preferred embodiments, the compound is capable of inhibiting the chloride ion current of the chloride channel protein; the compound is SITS and the chloride channel protein is expressed in breast cells. Preferably, the chloride channel protein consists essentially of the amino acid sequence shown in FIG. 1 (SEQ ID NO: 4).

In another aspect, the invention features a method of immunologically removing, from a biological sample, breast cancer cells which contain a polypeptide with at least 50% homology to the amino acid sequence shown in FIG. 1 (SEQ ID NO: 4) the method including the steps of:

a) contacting the biological sample with an antibody, preferably a monoclonal antibody, capable of specifically forming immune complexes with a polypeptide with at least 50% homology to the amino acid sequence shown in FIG. 1 (SEQ ID NO:4), where the polypeptide is capable of exhibiting a chloride ion current and is expressed in breast cells; where the contacting permits the specific formation of immune complexes between the antibody and any of the polypeptide containing cancer cells in the biological sample; and b) removing the complexes from the biological sample.

In preferred embodiments, the complexes are removed by contacting the complexes with a separable carrier which is an immunoglobin-conjugated bead, preferably, an IgG- or IgM-conjugated magnetic bead, and removing the complex-bound separable carrier from the biological sample; preferably the biological sample is from a human, preferably a human bone marrow, blood, or breast tissue sample.

In another aspect, the invention features a method of immunologically removing, from a biological sample, breast cancer cells which contain a polypeptide with at least 50% homology to the amino acid sequence shown in FIG. 1 (SEQ ID NO: 4), the method including the steps of:

a) contacting the biological sample with an antibody, preferably a monoclonal antibody, capable of specifically forming an immune complex with a polypeptide with at least 50% homology to the amino acid sequence shown in FIG. 1 (SEQ ID NO:4), where the polypeptide is capable of exhibiting a chloride ion current and is expressed in breast cells; where the contacting permits the specific formation of an immune complex between the antibody and any of the polypeptide containing cancer cells in the biological sample;

b) contacting the immune complex with complement, where the contacting is sufficient to cause complement-mediated lysis of the breast cancer cells.

In a preferred embodiment, the biological sample is from a human, preferably a human bone marrow, blood, or breast tissue sample.

In another aspect, the invention features a method of inhibiting the growth of breast cancer cells in a mammal, preferably a human, the method including administering to the mammal a therapeutic amount of a conjugate, which includes an antibody and a cytotoxin, preferably the antibody is a monoclonal antibody capable of forming an immune complex with a polypeptide consisting essentially of the amino acid sequence shown in FIG. 1 (SEQ ID NO:4), more preferably, the conjugate includes a monoclonal antibody capable of forming an immune complex with a polypeptide consisting of the amino acid sequence shown in FIG. 1 (SEQ ID NO:4).

In preferred embodiments, the cytotoxin is ricin, preferably blocked ricin, abrin, saporin, diphtheria toxin or a radionuclide.

In another aspect, the invention features a method of detecting breast cancer cells in a biological sample, the method including the steps of:

a) isolating RNA from the biological sample;

b) contacting the RNA with two opposed DNA oligonucleotide primers of opposite sense, each of which is at least 12 nucleotides in length, preferably the oligonucleotide primers are between 12 and 50 nucleotides in length (inclusive); where each of the primers includes a portion of a DNA sequence encoding a polypeptide with at least 50% homology to the amino acid sequence shown in FIG. 1 (SEQ ID NO:4) and being separated from each other by at least 30 nucleotides of the DNA sequence; where the polypeptide is capable of exhibiting a chloride ion current and is preferably expressed in breast cells;

c) performing, in the presence of the RNA and the primers, reverse transcription PCR (i.e., RT-PCR or RNA PCR); and d) detecting an increased level of amplified DNA product as an indication that the biological sample includes breast cancer cells.

In a preferred embodiment, the primer is labelled with one or more $^{32}P$, $^{33}P$, $^{35}S$ or fluorescently tagged nucleotides.

In another aspect, the invention features a method of isolating a DNA sequence encoding a polypeptide with at least 50% sequence homology to the amino acid sequence depicted in FIG. 1 (SEQ ID NO:4), the method including the steps of:

a) providing a cDNA library, preferably a phage, cosmid, or plasmid cDNA library made from human breast cells;

b) contacting the library with a single stranded oligonucleotide primer complementary to a portion of the DNA sequence depicted in FIG. 1 (SEQ ID NO:2), where the primer is either DNA or RNA and is at least 12 nucleotides in length, preferably between 12 and 50 nucleotides in length, inclusive, and the primer is labelled; where the contacting is under low stringency conditions which permit hybridization between the primer and the DNA sequence in the library;

c) detecting the hybridization and isolating the DNA from the library;

d) producing RNA from the DNA;

e) introducing the RNA into a cell, preferably a Xenopus oocyte, so that the cell subsequently expresses a polypeptide encoded by the RNA; and exhibits a chloride ion current; and f) detecting a chloride channel current from said cell, wherein said detecting is indicative of the isolation of said DNA.

In a preferred embodiment, the primer is labelled with one or more $^{32}P$, $^{33}P$, $^{35}S$ or fluorescently tagged nucleotides. The RNA is preferably introduced into the cell by injection. Alternatively, RNA may be introduced into the cell by electroporation, calcium-mediated precipitation, or projectile bombardment.

In addition, the nucleic acids depicted in SEQ ID NO:1 and FIG. 1 SEQ ID NO:2, or fragments thereof, can be used as nucleic acid probes in order to enable one of ordinary skill in the art of genetic engineering to identify and clone chloride channel protein homologs of human Mat-8 from any species, thereby expanding the usefulness of the DNA sequences of the invention.

As used herein, the term "substantially pure polypeptide" describes a polypeptide which has been separated from components which naturally accompany it. Typically, a polypeptide is substantially pure when at least 10% of the total material (by volume, by wet or dry weight, or by mole per cent or mole fraction) is a polypeptide of the invention. Preferably the polypeptide is at least 50%, more preferably at least 75%, even more preferably at least 90%, most preferably at least 99% of the total material. Purity can be conveniently assayed by well known methods such as SDS-PAGE gel electrophoresis, column chromatography, or HPLC analysis.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The term "isolated," as used herein, refers to a nucleic acid segment or fragment which is not immediately contiguous with (i.e., covalently linked to) both of the nucleic acids with which it is immediately contiguous in the naturally occurring genome of the organism from which the DNA is derived. The term, therefore, includes, for example, a DNA which is incorporated into a vector. For example, DNA can be incorporated into bacteriophage, virus (i.e. mammalian or insect virus) or plasmid vectors capable of autonomous replication in a eukaryotic, prokaryotic, or insect cell host. The term also includes a nucleic acid which exists as a separate molecule independent of other nucleic acids such as a nucleic acid fragment produced by chemical means, PCR, or restriction endonuclease treatment.

The term "degenerate variant" as used herein refers to a DNA sequence which is identical to the DNA sequence depicted in FIG. 1 (SEQ ID NO:2), except that the DNA sequence includes at least one nucleotide change which results in one or more alternative codons being used to encode the amino acid sequence depicted in FIG. 1 (SEQ ID NO:4). The art-skilled will appreciate that there are 61 codons for the 20 common amino acids so that many of the amino acids are encoded by more than one (i.e., alternative) codon (see Darnell et al. eds., Scientific American Books, Inc., 1986).

The term "homology" as used herein in reference to an amino acid sequence, refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

The term "consisting essentially of" as used herein, refers to amino acid sequence changes and/or non-sequence modifications, which do not affect the capability of the polypeptide depicted in FIG. 1 (SEQ ID NO:4) to exhibit a chloride ion current as defined by the experiments herein.

A "separable carrier" as used herein, refers to a synthetic composition which includes a pre-bound immunoglobin (e.g. IgG, IgA or IgM) moiety capable of binding an antibody. The carrier:antibody complex is conveniently separated from a sample because of a desirable physical property of the synthetic composition (e.g. weight, density or magnetism).

The term "increased level," as used herein, refers to the greater amount of immune complex or amplified DNA that is detected in a biological sample with breast cancer cells as opposed to a biological sample without breast cancer cells (i.e., a control sample).

By "specifically forming or binding" is meant an antibody which binds to a polypeptide of the invention or fragment thereof and which does not recognize and bind to antigenically-unrelated molecules as determined by Western blot.

BRIEF DESCRIPTION OF THE DRAWINGS

FIG. 1, Panel A is an illustration of the nucleotide and deduced amino acid sequence of the human Mat-8 gene. Panel B shows the partial nucleotide sequence of the 3.0 kb cDNA isolated from the SkBR-3 library referred to in the text. This sequence is contiguous with nucleotide 81 (arrow) of the DNA sequence shown in Panel A.

FIG. 3 is a protein sequence alignment and amino acid sequence comparison between the human and murine Mat-8 protein, canine PLM, and the sheep Na,K-ATPase γ-chain protein.

FIG. 5 is a set of four graphs (Panels A, B, C and D) showing membrane currents from Xenopus oocytes injected with murine Mat-8 mRNA.

DETAILED DESCRIPTION

Figure 2A:
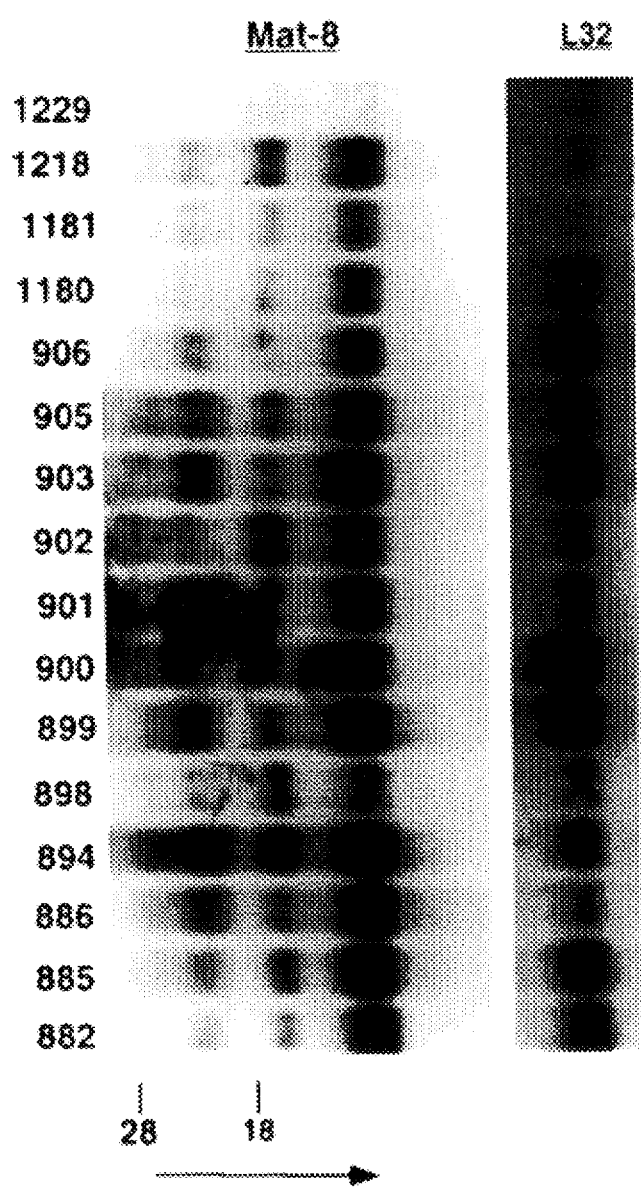
FIG. 2 is an RNA blot showing human Mat-8 gene expression in primary human breast tumor samples probed with a human Mat-8 cDNA probe (Panel A), or the human Mat-8 cDNA probe plus a ribosomal L32 probe (Panel B).

I. Isolation of the Human Mat-8 cDNA

Murine breast tumors were initiated by using the oncogenic transgenes c-neu or v-Hras according to standard methods. A cDNA corresponding to a transcript expressed in these murine breast tumors was identified. The cDNA, called Mat-8, was not expressed in mice bearing tumors initiated by the transgenic oncogene c-myc. The murine Mat-8 cDNA (SEQ ID NO:1) was labeled with [$\alpha$-$^{32}$P] dCTP by using the random hexamer technique (Feinberg, A. P., and Vogelstein, B. (1983) *Anal. Biochem.* 132:6–13). The labelled murine Mat-8 cDNA probe was used to screen a human breast cDNA library (Clonetech cat #HL1037b) by standard filter hybridization techniques (Sambrook et al. in *Molecular Cloning: A Laboratory Approach* (1988); Ausubel et al. *Current Protocols in Molecular Biology*, Green Publishing Associates and Wiley Intersciences (1993) ). For example, library filters were hybridized with the labelled murine Mat-8 cDNA probe in 10% Dextran sulfate, 48% formamide, 4.8× SSC (1× SSC is 0.15 sodium chloride, 0.015 sodium citrate), 20 mM Tris pH 7.5, 1× Denhardt's reagent, 20 mg/ml sheared herring sperm DNA combined with 1×10$^6$ cpm/ml of probe. Filters were washed in 2× SSC, 0.1% SDS at 55° C. for 1 hour. Positive clones were plaque purified, and phage DNA was prepared using standard techniques (Sambrook, J. et al. supra). By using this method, a single positive clone was isolated from the human breast cDNA library. The human cDNA insert was subcloned into the EcoRI site of the pBluescript™ SK vector (Stratagene Cloning Systems, La Jolla, Calif.), and double-stranded DNA was sequenced with a commercially available dideoxynucleotide DNA sequencing kit (Pharmacia Lkb Biotechnology, Inc.). DNA oligonucleotide primers complimentary to the human Mat-8 DNA sequence depicted in FIG. 1 (SEQ ID:2) can be made and used to probe a breast cell cDNA library in order to isolate the Mat-8 cDNA. Preferably, the oligonucleotide primers would be at least 12 nucleotides in length, more preferably between 12 and 50 nucleotides in length, inclusive. The DNA oligonucleotide primers can be labelled by well known methods at either the 5' end or internally labelled with radioactive or fluorescent nucleotides (see Sambrook et al. supra and Ausubel et al. supra).

In order to obtain additional clones, we made a cDNA library from the human breast tumor cell line SkbR-3 (available from American Type Culture Collection, Rockville, Md.). The SkbR-3 cDNA library was made by using the π-ZAP II™ vector according to the manufacturer's instructions (Stratagene). Approximately 10$^5$ unamplified phage were screened using a labelled human Mat-8 insert obtained by EcoRI digestion of the human Mat-8 cDNA clone. The SkbR-3 library was screened as described above, except filters were subjected to a more stringent wash (0.2× SSC, 0.1% SDS at 65° C. for 1 hour). After autoradiography, several positive plaques were identified and propagated. Positive phage isolates were rescreened and plaque-purified. Phagemid DNA was prepared according to rescue protocols provided by Stratagene.

Restriction enzyme digestion of each phage isolate revealed three distinct size-classes of clones. Analysis of seven clones revealed five that contained inserts of about 500 bp and one which contained approximately 1500 bp and 3000 bp of insert, respectively. All clones contained poly (A)+ tails. The complete DNA sequence of two independent clones representing the 500 bp class of cDNA insert was determined.

FIG. 1, Panel A shows the human Mat-8 cDNA sequence of the 509 bp insert, and immediately below, the deduced amino acid sequence. Nucleotides are numbered consecutively at the right and amino acids are numbered at the left. The data show a single open reading frame of 264 pairs flanked by 59 and 186 base pairs of 5'- and 3'-untranslated sequence, respectively. The putative leader sequence is underlined. The putative first amino acid of the mature protein was determined using the criteria of von Heijne (Steinmayer, K., et al. (1991) *Nature* 345, 301–304). The putative transmembrane domain in the figure is underlined twice; an imperfect polyadenylation signal is heavily underlined. Amino acid sequence surrounding the first methionine fits the consensus for translation initiation with the purine at position -3 (residue 57, see Kozak, infra). The putative initiation methionine is in a good Kozak consensus (Kozak, M. (1987) *Nucleic Acids Res* 15, 8125–8148) for translation initiation. Restriction mapping and partial sequence analysis of the 1500 bp insert clone identified approximately 800 bps of additional 3'-untranslated sequence, followed by a poly (A)$^+$ tail exactly at the point where the poly(A)$^+$ tail of the 509 bp clone begins. Thus, the 1500 bp clone reflects 3'end heterogeneity; a different polyadenylation signal is used. However, alternate polyadenylation signal usage does not effect the open reading frame shown in FIG. 1, Panel A. Note that the DNA sequence shown in FIG. 1, Panel A has an atypical polyadenylation signal, which probably accounts for the 3' end heterogeneity. The single clone containing a 3000 bp insert is identical to nucleotides 81 through 509 shown in FIG. 1, Panel A, including the use of the proximal polyadenylation site. However, the sequence of the 3 kb clone diverges at nucleotide 80 of FIG. 1, Panel A. This sequence at the 5' end of the cDNA is shown in FIG. 1, Panel B. The sequence removes the initiation methionine encoded by the Mat-8 cDNA and, instead, encodes alternative residues prior to residue 9 of Mat-8 (see FIG. 1, Panel A).

The human Mat-8 protein shown in FIG. 1, Panel A, has a leader sequence (amino acids 1 through 20). The mature protein contains 67 amino acids with a predicted molecular weight of approximately 8300 daltons. Amino acids 19–39 contain predominantly hydrophobic residues (with the exception of a cysteine at residues 24 and 29) which represent the single transmembrane domain of the protein. Given that many known ion channel proteins include multiple transmembrane domains (e.g., cystic fibrosis transmembrane regulator), the Mat-8 channel protein is structurally novel; it includes only a single transmembrane domain. The extracellular portion of the protein is acidic with a predicted pI of 5.3 and the intracellular portion is basic with a predicted pI of 8.3.

II. RNA Preparation and Northern Blot Analysis

Total RNA was isolated from various mouse tissues and human breast tumor cell lines by the method of Chirgwin et al. (Chirgwin, J. M., et al. (1979) *Biochemistry* 18, 5294–5299). Poly(A)$^+$ RNA was purified by oligo(dT)-cellulose chromatography as described by Pharmacia (Pharmacia Lkb Biotechnology, Inc.). RNA blot analysis was performed according to the procedure of Thomas (Thomas P. *PNAS* 77, 5201 (1981)) including transfer of the RNA to Genescreen™ membranes (Dupont). Human and murine Mat-8 cDNA probes were labeled with [α-$^{32}$P] dCTP by using the random hexamer technique, then hybridized to the RNA blots for phage screening as described above. Filters were washed in 0.2×SSC, 0.1% SDS at 65° C. for 1 hour.

Figure 2B:
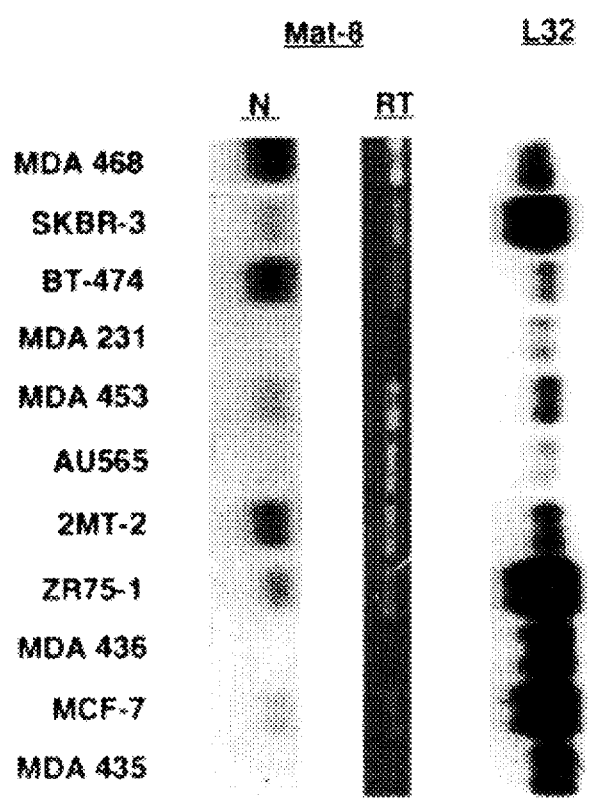

RNA blot analysis was performed by using the 509 bp human Mat-8 cDNA as a probe on RNA from primary human breast tumors and tumor cell lines (FIG. 2, Panels A and B). In FIG. 2, Panel A, sixteen primary tumor samples were analyzed by Northern blot. In Panel A, ten micrograms of total RNA was extracted from sixteen primary human breast tumors (Slamon, D. J. et al. (1989) *Science* 244: 707–712). The numbers 28 and 18 show the location of the 28S and 18S RNAs, respectively. The arrow shows the direction of RNA migration in the gel. All sixteen primary tumor samples were found to express the Mat-8 transcript. In all 16 tumor samples, three RNA species of 0.5 kb, 1.5 kb, and 3.0 kb were detected. In all cases, the 0.5 kb transcript was the major species detected. The data indicate that each of the 0.5 kb, 1.5 kb, and 3.0 kb cDNA clones isolated from the SkbR-3 cDNA library corresponds to an identically-sized mRNA detected in the RNA blot.

Analysis of the primary tumor samples can be complicated because tumors are mixtures of normal and malignant cells. In order to circumvent this potential problem, we performed Northern blots on human tumor cell lines. These cells were grown in Dulbecco's modified Eagle's medium supplemented with 10% bovine calf serum, 2 mM L-glutamine, 100 units/ml penicillin, and 10 mg/ml streptomycin, and total RNA was isolated by the method of Chirgwin, supra. In FIG. 2, panel B, ten micrograms of total RNA was extracted from each of several different human tumor cell lines (available from American Type Culture Collection, Rockville, Md.). The Northern blot depicted in FIG. 2, Panel B, shows that several breast cancer cell lines express the Mat-8 transcript (8 of 11 cell lines); the expression of Mat-8 transcript in the AU-565 cell line is present but does not reproduce well. The transcripts detected in the human tumor cell lines were of identical size to those found in primary breast tumor samples in Panel A. Only the predominant 0.5 kb transcript is shown in FIG. 2, Panel B.

The SkbR-3 and BT-474 cell lines are known to overexpress the Neu oncogene (Scott, G. K. et al. (1993) *Mol. Cell. Biol.* 13, 2247–2257; Hollywood, D. P., and Hurst, C. E. *EMBO J.* 12, 2369–2375). The MCF-7 and MDA 468 cell lines express normal levels of Neu and all four cell lines express Mat-8. Similarly, the above-described primary human tumors expressed Mat-8 (FIG. 2, Panel A), but only a subset overexpressed Neu (Slamon, D. J. et al. (1989) *Science* 244: 707–712). Potential correlations between Neu and Mat-8 expression may be explored by using antibodies disclosed herein.

i) Identification of the murine PLM cDNA: A cDNA encoding murine PLM was obtained by screening a commercially available mouse heart cDNA library (Clonetech) with a DNA oligonucleotide primer complementary to the dog PLM cDNA sequence (see FIG. 3 and Palmer et al. JBC 266, 11126 (1991)) by using standard filter hybridization techniques. DNA isolated from the Clonetech murine PLM cDNA was sequenced and the sequence used to design DNA oligonucleotide primers. The primers were used to obtain additional murine PLM cDNA clones by PCR. The products of the PCR reactions were radioactively labelled and used to probe murine and human RNA blots.

III. The Human Mat-8 Protein is Homologous to Phospholemman

A search of the nucleotide and protein data banks (Altschul, S. F. et al. (1990) *J. Mol. Biol.* 215, 403–410) revealed that the extracellular and transmembrane domains of the murine and human Mat-8 protein were homologous to those of the PLM protein. PLM is a chloride channel and the major plasmalemma substrate for cAMP-dependent protein kinase (PK-A) and protein kinase C (PK-C) in several different tissues. PLM contains consensus phosphorylation sites for both PK-A and PK-C in the cytoplasmic domain of the protein.

FIG. 3 shows an amino acid sequence alignment of human Mat-8, murine Mat-8, canine PLM and the γ-subunit of the sheep Na,K-ATPase. In the figure, a dash denotes identity between an amino acid in human Mat-8 and an amino acid in another protein. Amino acid sequences were aligned with the assistance of the Genetics Computer Group sequence analysis software (von Heijne, G. (1986) *Nucleic Acids Res* 14, 4683–4690). The transmembrane domain of human Mat-8 is underlined in the figure, and asterisks indicate putative PK-A and PK-C phosphorylation sites. The cytoplasmic domain of the murine and human Mat-8 gene were found to be unrelated to that of PLM and neither contains consensus phosphorylation sites, although serine 69 has a nearby lysine and could be a substrate for PKC. FIG. 3 also shows that canine PLM and Mat-8 contain acidic extracellular domains. The transmembrane domain of murine and human Mat-8, although conserved, is distinct from that of PLM by virtue of the presence of two cysteine residues. The nucleotide and protein database search also revealed homology between PLM, Mat-8, and the γ-subunit of Na,K-ATPase isolated from sheep kidney (Mercer, R. W. et al. (1993) *J. Cell Biol.* 121, 579–586). FIG. 3 shows that the homology between the γ-subunit and each chloride channel protein is confined to a portion of both the extracellular and transmembrane domains of each protein.

IV. Antibody Production and Immunological Detection of Mat-8 Protein

A peptide consisting of amino acids 2 through 17, inclusive, of the extracellular domain of murine Mat-8 (See FIG. 3) was synthesized according to standard synthetic methods (see Harlow and Lane in Antibodies: A Laboratory Approach CSHSQB (1988); Ausubel et al. supra) and coupled to KLH (Pierce cat #77107). Fifty micrograms of coupled peptide were used to inject a rabbit (Pocono Rabbit Farm) in order to produce polyclonal antisera. Various bleeds were tested for the presence of antisera which binds the murine Mat-8 peptide. The detection method employed a standard direct ELISA assay in which the Mat-8 peptide was coupled to BSA (Pierce cat #77107) on plates. Binding of the test sera to the plate was detected by using an alkaline phosphatase conjugated anti-rabbit sera. Prior to use, reactive Mat-8 antiserum was affinity purified using BSA coupled Mat-8 peptide and an Affigel solid matrix.

In order to demonstrate that murine Mat-8 could be expressed in Xenopus oocytes, 25 oocytes were injected with murine Mat-8 mRNA. The mRNA was produced in a standard transcription runoff experiment using an SP6 vector (Ambion). The injected oocytes were homogenized in 500 µl lysis buffer (50 mM Tris pH 7.5, 150 mM MaCL, 1% NP-40, 10 mM EDTA, 100 mg/ml PMSF) and 5 µl aliquots were run on a 15% SDS-polyacrylamide gel using a tris-tricine buffer system (Schagger, H. and von Jagow, G. (1987) Anal. Biochem. 166:368–373). As experimental controls, cell lysates were prepared from the mouse breast tumor cell line 16MB9a, which expresses murine Mat-8 mRNA at very low levels, and from SMF, which expresses at least 100-fold more Mat-8 mRNA than 16MB9a. SMF and 16MB9a cells ($5 \times 10^6$ cells each) were disrupted in lysis buffer (above) and 25 µl aliquots were analyzed a 15% SDS-PAGE gel. Electrophoresed proteins were transferred to Immobilon-P (Millipore), and the blot probed with the affinity purified anti-Mat-8 antibody. Antibody binding to the Mat-8 protein was detected by using a peroxidase-conjugated goat anti-rabbit IgG secondary antibody (Jackson ImmunoResearch Cat No: 11-035-003) and ECL reagents from Amersham.

Figure 4:
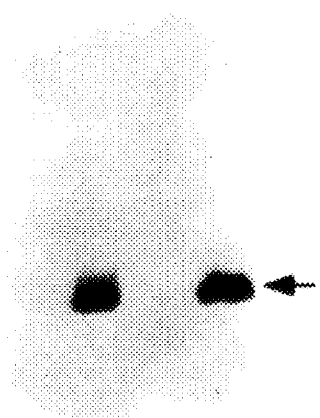
FIG. 4 is an immunoblot (i.e. Western blot) showing murine Mat-8 protein expression in Xenopus oocytes injected with murine Mat-8 RNA.

In FIG. 4, approximately one percent of a homogenate from 25 oocytes either uninjected (Lane 1) or injected with murine Mat-8 RNA (Lane 2) were electrophoresed, transferred to Immobilon-P, and incubated with affinity-purified antibody. Lysates from the mouse breast tumor cell lines 16MB9a (Lane 3) and SMF (Lane 4) are shown. Molecular weight markers are shown at left. The approximately 8 KD protein band corresponding to the Mat-8 channel protein is indicated by the arrow in FIG. 4. In a related experiment, mRNA from the human Mat-8 cDNA was prepared and injected into oocytes. The human Mat-8 protein produced by the oocyte was detectable with the affinity purified rabbit polyclonal antisera described above (immunoblot not shown).

Those skilled in the art will appreciate that a monoclonal antibody capable of binding the murine or human Mat-8 channel protein can be made by employing standard hybridoma technology. For example, monoclonal antibodies can be prepared using standard hybridoma technology (see, e.g., Kohler et al., *Nature* 256:495, 1975; Kohler et al., *Eur. J. Immunol.* 6:511, 1976; Kohler et al., *Eur J. Immunol.* 6:292, 1976; Hammerling et al., *In Monoclonal Antibodies and T Cell Hybridomas*, Elsevier, N.Y., 1981; Ausubel et al, supra; Harlow and Lane, supra).

V. The Mat-8 Protein is a Chloride Channel

Full-length PLM is poorly expressed in Xenopus oocytes, but removal of 5'-untranslated region greatly improves expression (Moorman, J. R. et al (1992) *J. Biol. Chem.* 267, 14551–14554). The 5'-untranslated region of murine Mat-8 was removed prior to expression in Xenopus oocytes. Standard PCR techniques were used to modify the full-length murine Mat-8 cDNA in order to insert a convenient Bgl-II restriction site immediately 5' and 3' of the cDNA sequence. A Bgl-II site was engineered 6 bps prior to the initiation methionine and a second Bgl-II site was added 3 bps beyond the stop codon. The modified murine Mat-8 cDNA was inserted into the Bgl-II site of the vector pSP64T (Kreig, P. A., and Melton, D. A. (1984) *Nucleic Acids Res.* 12, 7057–7070) to yield SP64T-Mat-8. The sequence of SP64T-Mat-8 was confirmed by standard dideoxy sequencing (see Sambrook et al. supra). The SP64T-Mat-8 vector was linearized with Sal-I and sense-capped mRNA transcripts were generated by using SP6 polymerase according to protocols provided by Ambion. Methods for Xenopus oocyte isolation, RNA injection, and microelectrode voltage clamping have been described (Moorman, J. R. et al. (1992) *J. Biol. Chem.* 267, 14551–14554; Durieux, M. E., et al. (1994) *Am. J. Physiol.* 263, C896–C900). Reversal potentials were measured from tail currents as previously described (Moorman, J. R., et al. (1992) *J. Biol. Chem.* 267, 14551–14554) and (Kowdley, G. C. et al. (1994) *J. Gen. Physiol.* 103, 217–230). The values of $[Cl^-]_o$, in mM, were 20, 36, 64, 112, and 200.

Injection of murine PLM RNA into Xenopus oocytes gives rise to a hyperpolarization-activated chloride current (Moorman, J. R. et al. (1992) J. Biol. Chem. 267, 14551–14554), thereby establishing PLM as a chloride channel protein. Given the homology between the PLM, the murine, and human Mat-8 amino acid sequences, Mat-8 must also function as a chloride channel protein. The following data support this idea by showing that murine Mat-8 expression induces a hyperpolarization-activated chloride current in injected Xenopus oocytes. As described above, the protein-coding region of murine Mat-8 was inserted into the translation vector pSP64T (Kreig, P. A., and Melton, D. A. (1984) *Nucleic Acids Res.* 12, 7057–7070) and used to transcribe Mat-8 RNA. Injection of murine Mat-8 RNA into Xenopus oocytes resulted in the expression of Mat-8 protein (as detected in a standard immunoblot (see FIG. 4)). Under voltage clamp, injected oocytes demonstrated large inward currents during hyperpolarization steps (FIG. 5, Panel B) which were not present in uninjected oocytes (FIG. 5, Panel A). The threshold for activation of the current was about −90 mV (FIG. 5, Panel C). The current-voltage relationship for oocytes injected with murine Mat-8 was virtually identical to oocytes expressing PLM (Moorman, J. R., et al. (1992) J. Biol. Chem. 267, 14551–14554). Currents induced by murine Mat-8 RNA injection were selective for $Cl^-$ ions. FIG. 5, Panel D shows the reversal potential of the current, measured from tail currents, as a function of $[Cl^-]_o$. As expected for a $Cl^-$ selective current, the reversal potential becomes more negative as $[Cl^-]_o$ increases. The straight line is the expected result for a perfectly selective $Cl^-$ current. The deviation of the data at low $[Cl^-]_o$ suggests that Mat-8 may be permeable to other ions.

Preliminary experiments have shown that chloride currents are observed with highly purified PLM molecules reconstituted into a synthetic lipid bilayer (data not shown).

a) Detailed Description of FIG. 5: Panels A and B show whole oocyte currents elicited using microelectrode voltage clamp steps from −10 mV (near the resting potential) to −30 to −160 mV. In uninjected oocytes there can be endogenous hyperpolarization-activated currents (Kowdley, G. C. et al. (1994) *J. Gen. Physiol.* 103, 217–230). In the experiments described herein, these endogenous currents were small. In oocytes injected with murine Mat-8 RNA, on the other hand, there were large inward currents during hyperpolarization steps. Panel C shows the current-voltage relationships for 14 oocytes from different frogs used to create the graphs in panels A and B. The threshold for activation of the current was about −90 to −100 mV. The inset shows a plot of normalized tail current amplitude at 40 mV as a function of the voltage of a 2 second conditioning prepulse. The straight line yields an estimated gating valence of 1.9 charges. Panel D shows the reversal potential of the current, measured from tail currents, as a function of $[Cl^-]_o$. As expected for a $Cl^-$ selective current, the reversal potential became more negative as $[Cl^-]_o$ was increased. The straight line was the expected result for a perfectly selective $Cl^-$ current. The deviation of the data at low $[Cl^-]_o$ suggests that other ions permeate murine Mat-8 as well.

The above-mentioned electrophysiological experiments which depict the chloride conductance properties of the murine Mat-8 channel protein can be repeated for the human Mat-8 channel protein by injecting human Mat-8 mRNA into oocytes instead of murine Mat-8 mRNA.

VII. Tissue Distribution of Mat-8 and Phospholemman Transcripts

Figure 6:
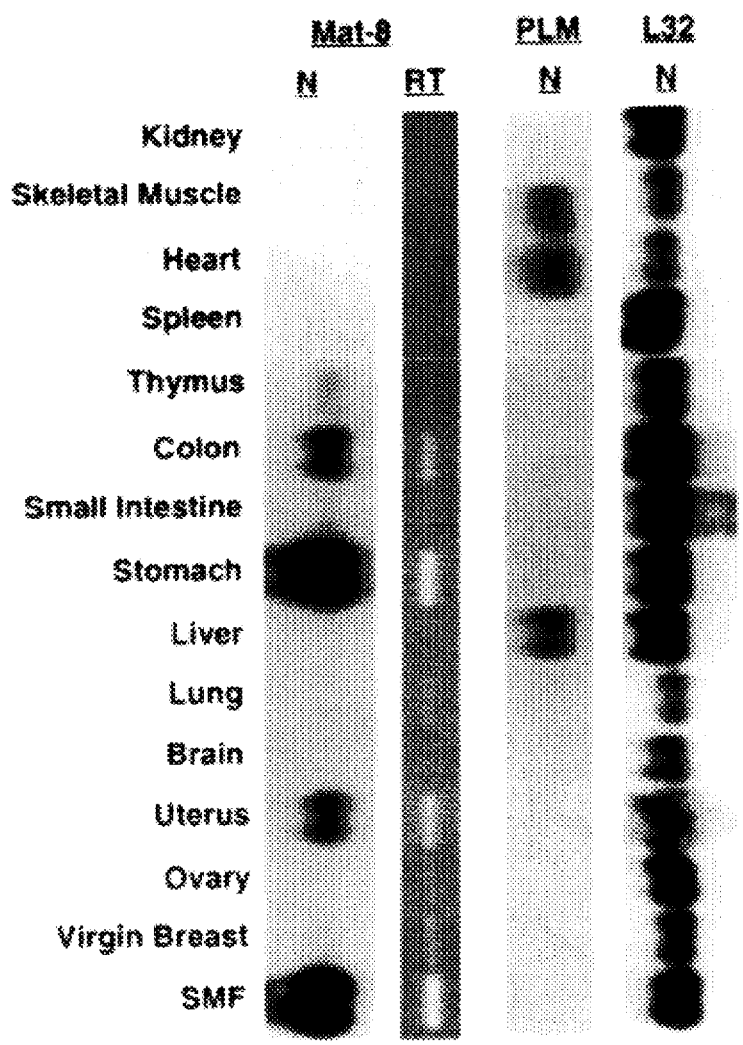
FIG. 6 is an RNA blot showing tissue-specific expression of murine Mat-8 and murine PLM.

RNA blot analysis was performed with mRNA isolated from several mouse tissues (FIG. 6). The RNA blot was probed with a labelled murine Mat-8 cDNA probe, a labelled murine PLM probe, and a labelled ribosomal protein L32 probe (Shen, M. M., and Leder, P. (1962) *Proc. Natl. Acad. Sci. USA* 89, 8240–8244), the latter as a control for RNA loading. Ten micrograms of total RNA was isolated from each organ of a virgin FVB/n mouse and the SMF cell line as described above. The RNA samples were electrophoresed, transferred to Genescreen™, and probed sequentially with the murine Mat-8 probe, murine PLM probe, and ribosomal L32 probe. The autoradiogram showed that PLM was expressed at high levels in the heart, skeletal muscle, and liver. PLM was expressed at lower levels in the breast, ovary, brain, lung, stomach, colon, and kidney. There was no expression of PLM in thymus, spleen, uterus, or the Neu-based breast tumor cell line, SMF. The Mat-8 protein, conversely, was expressed at high levels in the SMF line, uterus, stomach, colon, and at lower levels in virgin breast, ovary, lung, small intestine, and thymic stroma. In contrast to PLM, Mat-8 was not expressed in liver, heart, or skeletal muscle.

Thus, PLM and Mat-8 display distinct tissue specific patterns of gene expression that indicate distinct cellular functions. The expression of murine Mat-8 in the breast, lung, stomach, and colon implicates this channel protein in transepithelial transport. Conversely, the high-level expression of PLM in the heart or skeletal muscle suggests functions distinct from Mat-8. Moreover, PLM is regulated by phosphorylation, whereas there is no evidence for phosphorylation regulation of Mat-8.

VIII. Isolation of the Human Mat-8 Chloride Channel Protein

The human Mat-8 channel protein can be isolated using a Mat-8 antibody, preferably a Mat-8 monoclonal antibody, and standard immunoprecipitation techniques. For example, Mat-8 monoclonal antibody can be covalently bound to activated sepharose beads and the beads used to isolate the Mat-8 channel protein from a cell line which expresses Mat-8 (e.g. SMF cell line). The purification of proteins by immunoprecipitation techniques has been described (Ausubel et al., supra; Harlow and Lane, supra). Alternatively, the human Mat-8 cDNA can be inserted into a prokaryotic, eukaryotic, or insect cell expression vector, the cDNA can be expressed, and the human Mat-8 protein purified, as disclosed in Ausubel et al., supra; Sambrook et al., supra; and Summer and Smith, *A Manual of Methods for Baculovirus Vectors and Insect Cell Culture Procedures:* Texas Agricultural Experimental Station Bulletin No. 1555, College Station, Tex. (1988).

IX. Identification of Compounds that Modulate Human Mat-8 Channel Activity

Chloride channel proteins are needed to maintain the function of breast cells. Compounds that modulate chloride channel activity, for example, compounds which inhibit chloride ion current, will interfere with the function of breast cells, particularly breast cancer cells. Therefore, breast cell chloride channel proteins will provide a novel therapeutic target for the treatment of breast cancer. In order to screen for compounds which modulate the activity of the Mat-8 chloride channel protein, murine Mat-8 mRNA was injected into Xenopus oocytes and the chloride ion current detected as described above. After injection and expression of the murine Mat-8 channel protein, 1 mM of the chloride channel blocker SITS (i.e. 4-acetamido-$4^1$-isothiocyanostilbene-2,2$^1$ disulfonic acid, see Gogelein, H. supra) was added to the oocyte medium. The chloride ion current exhibited by the injected oocytes was compared before and after addition of SITS in order to evaluate whether the compound was capable of modulating the activity of the expressed Mat-8 channel protein. The results of these experiments have shown that 1 mM of SITS inhibits the activity of the Mat-8 chloride channel in injected oocytes. This result is similar to recent work showing that PLM is inhibited by millimolar amounts of either SITS, DIDS, bumetanide, or niflumic acid (Kowdley et al., supra).

In addition to SITS, many compounds can be screened for the ability to modulate the activity of the human Mat-8 channel protein. These compounds include DIDS; DPC; NPPB; polycyclics, including anthracene-9-carboxylic acid; diazepam; pentylenetetrazol; picrotoxin; benzoates; including furosemide; phenoxyacetates, including ethacrynic acid; sulfonates and sulfamides, including disulfonic stilbenes such as SITS; bicuculline; bicyclic phosphates; several insecticides; strychnine and related compounds; flufenamic acid and related compounds; arylaminobenzoates, including diphenylamine-2-carboxylate; 2-(2-furfurylmethylamino)5-nitrobenzoic acid; 4-Chloro-3-N-pyrrolidino-benzoic acid; 3-((2-anilino-5-nitro-phenyl)sulfonyl)-1-isopropyl urea; bumetanide; clofilium; derivatives of phenoxyacetic acid, and niflumic acid (Gogelien, H. supra; Greger, R. supra; Attall, B. et al. *Nature* 365, 850 (1993); Kowdley et al., supra, and references cited therein). In order to test other compounds for the capacity to modulate human Mat-8, 1 mM of a compound is dissolved in an appropriate solvent (i.e., water, oocyte medium, ethyl alcohol, DMSO etc.) and is added to the medium of murine Mat-8 injected oocytes. The oocytes are injected with human Mat-8 mRNA prepared as described above. The effect of the compound on the human Mat-8 chloride ion current is then evaluated. The screen will identify reagents, like SITS, which are capable of inhibiting the chloride ion current exhibited by the human Mat-8 channel protein.

X. Identification of Compounds that Modulate the growth of Mat-8 Expressing Cells i) Cell culture assay: Compounds that modulate the activity of the Mat-8 chloride channel, for example, SITS as described above (see IX) can be tested for the ability to modulate the growth of cells which express the Mat-8 protein. This is accomplished by obtaining control cells such as NIH3T3 fibroblasts which do not express Mat-8 and comparing them with NIH3T3 fibroblasts transfected with a vector which includes the human Mat-8 cDNA. Generally, any commercially available eukaryotic expression vector can be used to drive expression of human Mat-8 in NIH3T3 cells. As an example, 1 mM of SITS can be added to the growth medium of transfected fibroblasts which express the Mat-8 channel protein. Alternatively, the growth of human breast tumor cell lines which express Mat-8 (described above) can be examined after exposure to SITS. Growth modulation is conveniently assayed after 24–72 hours of exposure to SITS by standard techniques. For example, these techniques include determining the incorporation of radioactive nucleotides into cell DNA or evaluating cell viability (e.g., trypan blue staining) after exposure to SITS. The experiment can be repeated with other compounds that show a capacity to modulate the chloride ion current of the human Mat-8 channel protein (see IX, above).

ii) Tumor model assay: Reagents which modulate the chloride ion current of the Mat-8 chloride channel (see IX) and modulate the growth of human breast tumor cells and/or NIH3T3 fibroblasts engineered to express Mat-8 (above), can be tested for the ability to inhibit tumor growth in mice. For example, a mouse or human breast tumor cell line (e.g. SMF, SK-BR3, MDA-468) can be delivered subcutaneously or into the mammary fat pad of the mouse in order to establish a tumor. After establishing a tumor in a mouse, a compound which has been shown to modulate human Mat-8 chloride channel activity in Xenopus oocytes (see IX), and/or fibroblasts (see i, above), is then administered to the tumor-bearing mouse. Methods for administering compounds are described below. A compound that inhibits the growth of the mouse tumor and does not have any obvious toxic side effects in the mouse can be administered to humans who are at risk of, or suffering from, breast cancer.

XI. Administration

A compound capable of modulating the chloride ion current of the Mat-8 chloride channel can be formulated into a pharmaceutical composition by admixture with pharmaceutically acceptable nontoxic excipients and carriers. Such compositions may be prepared for use in parenteral administration, particularly in the form of liquid solutions or suspensions; for oral administration, particularly in the form of tablets or capsules; or intranasally, particularly in the form of powders, nasal drops, or aerosols.

The composition is conveniently administered in unit dosage form and may be prepared by any of the methods well known in the pharmaceutical art, or example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylenepolyoxypropylene copolymers can be useful excipients to control the release of the compound. Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

Compounds can be employed as the sole active agent in a pharmaceutical or can be used in combination with other compounds and/or with chemotherapeutic therapies (e.g. radiation, cytotoxic drugs).

The concentration of a compound described herein in a therapeutic composition will vary depending upon a number of factors, including the dosage of the reagent to be administered, the chemical characteristics (e.g., hydrophobicity) of the compounds employed, and the route of administration. In general terms, the reagent is provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the breast cancer, the overall health status of the particular patient, the relative biological efficacy of the reagent selected, the formulation of the compound excipients, and its route of administration.

XII. Immunological Removal (i.e., Purging) of Breast Tumor Cells from a Patient Sample An important concern accompanying the introduction of an autologous cell sample into a cancer patient undergoing chemotherapy is the re-introduction of neoplastic cells (Soiffer, R. J. et al. *Bone Marrow Transplantation* 12, 243 (1993); Gribbens et al. *Blood* 80, 1083 (1992)). For example, Gribbens et al. supra have described the dangers of re-infusing autologous bone marrow cells into patients treated for various cancers; the introduced bone marrow cells may include neoplastic cells. Since breast cancer cells express high levels of the Mat-8 channel protein, such cells can be removed from the sample. In order to remove breast cancer cells from a bone marrow sample, a bone marrow sample is incubated in physiological buffer with a monoclonal antibody that binds the Mat-8 chloride channel protein (37° C. for 30 minutes). After binding of the monoclonal antibody to the breast cancer cells, the breast cancer cells can be conveniently removed by either complement lysis or binding the monoclonal antibody (bound to breast cancer cells) to immunomagnetic beads as described by Gribbens et al. supra, and references therein.

XIII. Mat-8 Antibody:Toxin Conjugates

Monoclonal antibodies can be linked to cytotoxic drugs such as ricin, abrin, saporin and diphtheria toxin (see also U.S. Pat. No. 5,055,291), or radionuclides. Such monoclonal antibody conjugates are clinically useful in the treatment of cancer. For example, monoclonal antibody:ricin conjugates have been used in the serotherapy of B-cell neoplasms, especially as follow-up therapy to autologous bone marrow transplant (Grossbard, M. L. et al. *Blood* 79, 576 (1992); Grossbard, M. L. et al. *Blood* 81, 2263 (1993)). A Mat-8 antibody:ricin conjugate is made by crosslinking a Mat-8 monoclonal antibody with blocked ricin (i.e., Mat-8: ricin conjugate) as described in Grossbard, M. L. supra. The effectiveness of the Mat-8:ricin conjugate can be evaluated by adding the conjugate to primary human breast cancer cells, and separately, adding the conjugate to human breast cancer cell lines as described herein. Generally, about 1 µg to 100 µg of conjugate is added per 1 ml of cell medium. After 24–72 hours, such treated cells are washed with PBS and added to fresh medium and the fraction of surviving cells determined by the method of Grossbard, M. L. supra. If the Mat-8:ricin conjugate is capable of killing breast cancer cells, as opposed to control cells which do not express the Mat-8 protein such as NIH3T3 fibroblasts, the conjugate can be administered to patients suffering, or who are at risk of suffering from breast cancer. The administration of a monoclonal antibody:blocked ricin conjugate to a human patient has been described (Grossbard, M. L. supra).

XIV. Detection of Breast Cancer Cells by RT-PCR

Hematologic malignancies such as lymphomas are associated with chromosomal abnormalities. These abnormalities are readily detectable by PCR in bone marrow or peripheral blood (see Gribben, J. G. et al. supra). However, unlike hematologic malignancies, breast cancers do not exhibit any common chromosomal abnormalities. If the Mat-8 gene is expressed in breast cancer cells and not in bone marrow or blood cells, then RNA can be isolated from bone marrow or blood and the isolated RNA used to perform reverse transcription-PCR (i.e., RT-PCR or RNA PCR; see Innis et al., *PCR Protocols*, Academic Press, Inc., Harcourt Brace Jovanovich Publishers; Erlich, *PCR Technology*, Stockton Press). If a DNA amplification product is detected by RT-PCR, then the result would indicate that breast cells are present in the sample. In general, at least two DNA oligonucleotide primers complementary to the human Mat-8 sequence (SEQ ID NO:2) and opposed to each other can be designed and used to detect Mat-8 expression in blood or bone marrow samples isolated from normal individuals and patients with breast cancer. Such primers generally are at least 12 nucleotides in length, preferably between 12 and 50 nucleotides in length and are separated from each other by at least 30 bp of intervening Mat-8 DNA (see FIG. 1). If the RT-PCR reaction is negative in bone marrow or blood cells obtained from normal patients, but positive in a patient with breast cancer, the method would provide a convenient, simple and sensitive method for the early detection of breast cancer.

XV. Identification of Breast Cell Chloride Channel Proteins Related to Human Mat-8

Ion channel proteins that are related to each other often exhibit mRNA transcript heterogeneity. The results shown herein suggest that the human Mat-8 chloride channel protein exhibits transcript heterogeneity. It would be useful to obtain cDNAs that encode channel proteins which are related (i.e., at least 50% homologous at the protein level) to the human Mat-8 protein. These cDNAs, each representing a distinct chloride channel protein, could then be used to screen for new compounds that modulate the chloride ion current of breast cells. A comprehensive screen for new compounds that modulate the activity of the Mat-8 chloride channel protein and other related chloride channel proteins, would uncover therapeutically useful compounds that modulate the function of breast cells, particularly breast cancer cells. Preferably, the screen would uncover compounds that inhibit the chloride ion conductance of breast cancer cells.

Breast cell chloride channel proteins that are at least 50% homologous to the human Mat-8 protein sequence (FIG. 1) can be identified by standard filter hybridization techniques. For example, DNA or RNA oligonucleotide primers that are complementary to the DNA sequence depicted in FIG. 1 (SEQ ID NO:2) or a Mat-8 cDNA restriction fragment (e.g., EcoRI cut fragment) can each be employed to screen for Mat-8 homologs. Alternatively, degenerate oligonucleotide primers may be designed by well-known methods and used to detect Mat-8 homologs. The oligonucleotide primers will be between 12 and 50 nucleotides in length, inclusive. The oligonucleotide primers will be radioactively labelled (i.e., 5' end labelled) and used to screen a cDNA library (e.g., phage or cosmid libraries prepared from breast tissue) or a genomic library. The breast cell cDNA libraries described herein can be used to screen for related chloride channel proteins, although other commercially available genomic or cDNA libraries can also be used. The screen is performed at reduced (i.e., low) stringency conditions in order to identify DNA sequences in the library which are at least 50% identical to the oligonucleotide primer. In general, low stringency hybridization techniques detect DNA sequences which are approximately 50% homologous (at the DNA level) to a particular probe. For a discussion on performing a screen under low stringency conditions see Sambrook et al., supra; Ausubel et al. supra; Hames, B. D. and Higgins, S. J. in *Nucleic Acid Hybridization: A Practical Approach* IRL Press (1985). As an example, low stringency conditions for detecting DNA sequences which are at least 50% identical to the DNA sequence shown in FIG. 1 (SEQ ID NO:2) include hybridization at about 42° C. with about 6× SSC and about 1% SDS; and a second wash at about 50° C. with about 6× SSC and about 1% SDS. Low stringency conditions for use with a particular oligonucleotide primer restriction fragment, or set of primers is conveniently established by first performing a Northern or Southern blot hybridization with library DNA and a labelled oligonucleotide primer. Phage or cosmid clones which hybridize to a labelled oligonucleotide primer under low stringency conditions, but not at high stringency conditions, are good candidates for encoding proteins related to the Mat-8 chloride channel protein. Of course, some clones may share extensive DNA homology with the human Mat-8 DNA sequence and accordingly, will hybridize at both low and high stringency conditions. As an example, high stringency conditions include hybridization at about 42° C. and about 50% formamide; a first wash at about 65° C., about 2× SSC, and 1% SDS; followed by a second wash at about 65° C. and about 0.1% SSC. Positive clones can be DNA sequenced by standard methods and conceptually translated by the methods used herein. As described above for the murine Mat-8 chloride channel protein, RNA can be made from a chloride channel cDNA related to Mat-8 and introduced into Xenopus oocytes. The RNA injected oocytes can then be tested for the expression of a chloride ion current as described above.

ADDITIONAL EMBODIMENTS

The invention also features breast cell chloride channel proteins whose amino acid sequence differs from the amino acid sequence shown in FIG. 1 (SEQ ID NO:2) by one or more conservative amino acid substitutions, for example, substitution of one amino acid for another with similar characteristics (e.g. valine for glycine, arginine for lysine etc.) or by one or more non-conservative amino acid substitutions, deletions or insertions which do not materially affect or otherwise abolish the chloride ion current of the channel protein. A list of conservative amino acid replacements is shown below:

CONSERVATIVE AMINO ACID REPLACEMENTS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Proline | P | D-Pro, L-1-thioazolidine-4-carboxylic acid, D-or L-1-oxazolidine-4-carboxylic acid (Kauer, U.S. Patent (4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Other channel protein modifications include those which increase channel protein stability; for example, by the introduction of one or more non-peptide bonds (which replace the peptide bonds) or D-amino acids in the polypeptide. Chloride channel proteins can differ from the amino acid sequence of FIG. 1 (SEQ ID NO:2) in amino acid sequence or by modifying the protein in ways that do not involve sequence, or both. Non-sequence modifications of channel proteins include in vivo or in vitro chemical derivatization of peptides, e.g., acetylation, methylation, phosphorylation, carboxylation, myristylation or glycosylation. Also included are chloride channel proteins that include residues other than naturally occurring L-amino acids, e.g., D-amino acids or non-naturally occurring or synthetic amino acids, e.g., β or γ amino acids. Alternatively, increased stability may be conferred by cyclizing the chloride channel protein.

It will be readily apparent to those skilled in the art that the above-described compositions and methods can be used as a diagnostic kit suitable for clinical use. Such a kit would include an antibody capable of specifically forming an immune complex with a polypeptide with at least 50% homology to the amino acid sequence depicted in FIG. 1 (SEQ ID NO: 4), and a polypeptide of the invention. Preferably, the antibody is a monoclonal antibody capable of specifically forming an immune complex with a polypeptide which consists of the amino acid sequence depicted in FIG. 1 (SEQ ID NO: 4). The kit may also include two or more oligonucleotide primers of at least 12 bp in length, preferably 12 to 50 bp inclusive, which are complementary to a portion of the DNA sequence depicted in FIG. 1 (SEQ ID NO: 2) and are suitable for RT-PCR.

All publications and patent applications mentioned in the specification are indicative of the level of skill of those in the art to which this invention pertains. All publications and patent applications are incorporated herein by reference to the same extent as if each individual publication or patent application were specifically and individually stated to be incorporated by reference.

Although the foregoing invention has been described in some detail by way of illustration and example for the purposes of clarity of understanding, one skilled in the art will easily ascertain that certain changes and modifications may be practiced without departing from the spirit and scope of the appended claims.

What is claimed is:

1. An isolated DNA comprising a DNA sequence encoding a polypeptide consisting of a first amino acid sequence, said first amino acid sequence shown in FIG. 1 (SEQ ID NO:4) or a second amino acid sequence which differs from said first amino acid sequence by one or more conservative substitutions, said first or said second amino acid sequence being capable of conducting a chloride ion current.

2. An isolated DNA of claim 1, wherein said DNA is a DNA sequence encoding a polypeptide consisting of the amino acid sequence shown in FIG. 1 (SEQ ID NO:4).

3. The isolated DNA of claim 2, wherein said polypeptide is expressed in breast cells.

4. A vector comprising the isolated DNA of claim 2.

5. Substantially pure DNA having the nucleic acid sequence of FIG. 1 (SEQ ID NO:2), or degenerate variants thereof, and encoding the amino acid sequence shown in FIG. 1 (SEQ ID NO:4).

6. Substantially pure DNA which a) is capable of hybridizing to the DNA sequence of FIG. 1 (SEQ ID NO:2) after a wash in 0.2×SSC and 0.1% SDS at 65° for an hour; b) encodes a polypeptide capable of conducting a chloride ion current; and c) encodes a polypeptide expressed in breast cells.

7. A cell comprising the isolated DNA of claim 2.

8. A cell comprising the vector of claim 4.

9. The cell of claim 7 or 8, wherein said cell expresses said polypeptide and exhibits a chloride ion current.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 522
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GGCAAGTCCA  TTCTCTGCTT  TCTCCCGGAA  CCACCTCTCA  GCCTGTTGAG  CTACTCAGGT      60

CAAGGCTTTG  AC                                                              72

ATG  CAA  GAG  GTT  GTT  CTG  AGC  CTG  TTG  GTC  CTT  CTA  GCA  GGC  CTG  CCT     120
Met  Gln  Glu  Val  Val  Leu  Ser  Leu  Leu  Val  Leu  Leu  Ala  Gly  Leu  Pro
```

```
     1                    5                        10                        15
ACT  TTG  GAT  GCC  AAT  GAC  CCT  GAA  AAT  AAA  AAT  GAT  CCT  TTC  TAC  TAT    168
Thr  Leu  Asp  Ala  Asn  Asp  Pro  Glu  Asn  Lys  Asn  Asp  Pro  Phe  Tyr  Tyr
               20                       25                       30

GAT  TGG  TAC  AGC  CTC  CGA  GTC  GGC  GGG  CTC  ATT  TGT  GCA  GGG  ATT  CTC    216
Asp  Trp  Tyr  Ser  Leu  Arg  Val  Gly  Gly  Leu  Ile  Cys  Ala  Gly  Ile  Leu
               35                       40                       45

TGT  GCC  CTG  GGC  ATT  ATA  GTC  CTT  ATG  AGT  GGC  AAA  TGC  AAA  TGC  AAG    264
Cys  Ala  Leu  Gly  Ile  Ile  Val  Leu  Met  Ser  Gly  Lys  Cys  Lys  Cys  Lys
     50                            55                       60

TTC  AGA  CAG  AAA  CCC  AGT  CAC  CGC  CCA  GGA  GAA  GGG  CCA  CCT  CTC  ATC    312
Phe  Arg  Gln  Lys  Pro  Ser  His  Arg  Pro  Gly  Glu  Gly  Pro  Pro  Leu  Ile
65                       70                       75                       80

ACA  CCA  GGC  TCA  GCT  CAC  AAC  TGC  TGA                                       339
Thr  Pro  Gly  Ser  Ala  His  Asn  Cys
                    85

AGATGGACCA  GTTAAAAGAG  CACAGGTCCT  GGCTCTGAAG  GTGGGCTTGA  ACTCCGAGCT            399

GGCTGTTCTC  CTCCCCTCCT  GACACTGCCT  TCCCCGAGCC  TCATCTCACC  CCTCGTGGTA            459

GCAGGCTCTT  TGTTCAGTTT  TTAATATAAA  ATGATTCAC  ATCAAAAAAA  AAAAAAAAA              519

AAA                                                                               522
```

( 2 ) INFORMATION FOR SEQ ID NO: 2:

( i ) SEQUENCE CHARACTERISTICS:
      ( A ) LENGTH: 526
      ( B ) TYPE: nucleic acid
      ( C ) STRANDEDNESS: single
      ( D ) TOPOLOGY: linear ( x i ) SEQUENCE DESCRIPTION: SEQ ID NO: 2:

```
CCCGATTTCT  CCCGGAACCT  CTGCTCAGCC  TGGTGAACCA  CACAGGCCAG  CGCTCTGAC              59

ATG  CAG  AAG  GTG  ACC  CTG  GGC  CTG  CTT  GTG  TTC  CTG  GCA  GGC  TTT  CCT    107
Met  Gln  Lys  Val  Thr  Leu  Gly  Leu  Leu  Val  Phe  Leu  Ala  Gly  Phe  Pro
1                   5                        10                       15

GTC  CTG  GAC  GCC  AAT  GAC  CTA  GAA  GAT  AAA  AAC  AGT  CCT  TTC  TAC  TAT    155
Val  Leu  Asp  Ala  Asn  Asp  Leu  Glu  Asp  Lys  Asn  Ser  Pro  Phe  Tyr  Tyr
               20                       25                       30

GAC  TGG  CAC  AGC  CTC  CAG  GTT  GGC  GGG  CTC  ATC  TGC  GCT  GGG  GTT  CTG    203
Asp  Trp  His  Ser  Leu  Gln  Val  Gly  Gly  Leu  Ile  Cys  Ala  Gly  Val  Leu
               35                       40                       45

TGC  GCC  ATG  GGC  ATC  ATC  ATC  GTC  ATG  AGT  GCA  AAA  TGC  AAA  TGC  AAG    251
Cys  Ala  Met  Gly  Ile  Ile  Ile  Val  Met  Ser  Ala  Lys  Cys  Lys  Cys  Lys
     50                            55                       60

TTT  GGC  CAG  AAG  TCC  GGT  CAC  CAT  CCA  GGG  GAG  ACT  CCA  CCT  CTC  ATC    299
Phe  Gly  Gln  Lys  Ser  Gly  His  His  Pro  Gly  Glu  Thr  Pro  Pro  Leu  Ile
65                       70                       75                       80

ACC  CCA  GGC  TCA  GCC  CAA  AGC  TGA                                            323
Thr  Pro  Gly  Ser  Ala  Gln  Ser
                    85

GGACAGACCA  GCTGAAATTG  GGTGGAGGAC  CGTTCTCTGT  CCCCAGGTCC  TGTCTCTGCA            383

CAGAAACTTG  AACTCCAGGA  TGGAATTCTT  CCTCCTCTGC  TGGGACTCCT  TTGCATGGCA            443

GGGCCTCATC  TCACCTCTCG  CAAGAGGGTC  TCTTTGTTCA  ATTTTTTTA  ATCTAAAATG             503

ATTAAAAAAA  AAAAAAAAA  AAA                                                        526
```

( 2 ) INFORMATION FOR SEQ ID NO: 3:

( i ) SEQUENCE CHARACTERISTICS:
      ( A ) LENGTH: 45

(B) TYPE: nucleic acid
    (C) STRANDEDNESS: single
    (D) TOPOLOGY: linear (xi) SEQUENCE DESCRIPTION: SEQ ID NO: 3:

TGAGCCTGGG ATAGCTGACA TCAGTGGGCT GCTCGAGCCG TGCTT        45

(2) INFORMATION FOR SEQ ID NO: 4:

(i) SEQUENCE CHARACTERISTICS:
        (A) LENGTH: 87
        (B) TYPE: amino acid
        (C) STRANDEDNESS: single
        (D) TOPOLOGY: linear (xi) SEQUENCE DESCRIPTION: SEQ ID NO: 4:

```
Met Gln Lys Val Thr Leu Gly Leu Leu Val Phe Leu Ala Gly Phe Pro
1               5                   10                  15

Val Leu Asp Ala Asn Asp Leu Glu Asp Lys Asn Ser Pro Phe Tyr Tyr
            20                  25                  30

Asp Trp His Ser Leu Gln Val Gly Gly Leu Ile Cys Ala Gly Val Leu
        35                  40                  45

Cys Ala Met Gly Ile Ile Ile Val Met Ser Ala Lys Cys Lys Cys Lys
    50                  55                  60

Phe Gly Gln Lys Ser Gly His His Pro Gly Glu Thr Pro Pro Leu Ile
65                  70                  75                  80

Thr Pro Gly Ser Ala Gln Ser
                85
```